(12) United States Patent
Comings et al.

(10) Patent No.: US 6,653,073 B1
(45) Date of Patent: Nov. 25, 2003

(54) ASSOCIATION OF THE SEROTONIN TRANSPORT (HTT) GENE WITH CARDIOVASCULAR DISEASE AND LONGEVITY

(75) Inventors: David E. Comings, Duarte, CA (US); James P. MacMurray, Loma Linda, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/622,503

(22) PCT Filed: Feb. 19, 1999

(86) PCT No.: PCT/US99/03700

§ 371 (c)(1), (2), (4) Date: Dec. 4, 2000

(87) PCT Pub. No.: WO99/42619

PCT Pub. Date: Aug. 26, 1999

Related U.S. Application Data

(60) Provisional application No. 60/075,613, filed on Feb. 20, 1998, and provisional application No. 60/110,150, filed on Nov. 25, 1998.

(51) Int. Cl.[7] .......................... C07H 21/04; C12Q 1/68
(52) U.S. Cl. .......................... 435/6; 435/91.1; 536/23.1
(58) Field of Search .................... 435/6, 91.1; 536/23.1

(56) References Cited

U.S. PATENT DOCUMENTS

| | | | | |
|---|---|---|---|---|
| 5,401,498 A | * | 3/1995 | Kesseler et al. | 424/78.11 |
| 5,417,863 A | * | 5/1995 | Varady et al. | 210/635 |
| 5,418,162 A | | 5/1995 | Blakely et al. | |
| 6,132,724 A | * | 10/2000 | Blum | 424/195.1 |
| 6,242,181 B1 | * | 6/2001 | Siffert | 435/6 |
| 6,245,527 B1 | * | 6/2001 | Busfield et al. | 435/69.1 |

FOREIGN PATENT DOCUMENTS

| WO | WO 99/42619 | 9/1999 |
|---|---|---|

OTHER PUBLICATIONS

Little et al. Am. J. PSychiatry, vol. 155, No. 2, pp. 207–213, Feb. 1998.*

Brow, "Sequencing with Taq DNA polymerase" PCR Protocols: A Guide to Methods and Applications, pp. 189–196, 1990.*

Community Outreach Health Information System. www.b-u.edu/cohis/cardvasc/dislist.htm, Nov. 27, 2001.*

Lesch et al. "Association of anxiety–related traits with a polymorphism in the serotonin transporter gene regulatory region". Science, vol. 272, pp. 1527–1531, Nov. 1996.*

Nakamura et al. "Serotonin Transporter gene regulatory region polymorphism and anxiety –related traits in the Japanese". Am. J. of med. Genetics. vol. 74, No. 5, pp. 544–545, Sep. 1997.*

Li et al. "Alleleic functional variation of serotonin transporter expression is a susceptibility factor for late onset Alzheimer's disease". Neuroreport vol. 8, No. 3, pp. 683–686, Feb. 1997.*

Carney, R. et al., "Depression and Coronary Heart Disease: A Review for Cardiologists", *Clin. Cardiol.*, 1997, vol. 20., pp. 196–200.

Robertson, J.I.S., "Serotonin, Serotonin Antagonists, Hypertension and Vascular Diseases", *Current Opinion in Cardiology*, 1988, vol. 3, pp. 702–714.

Glassman, A. et al., "Review of the Cardiovascular Effects of Heterocyclic Antidepressants", *J. Clin. Psychiastry*, 1993, vol. 54., No. 2, pp. 16–22.

Engelberg, H. et al., "Low Serum Cholesterol and Suicide", *The Lancet*, 1992, vol. 339, pp. 727–729.

Smith, C.C.T. et al., Reduced Platelet Serotonin Content and Release in Familial Hypercholesterolaemia, *Atherosclerosis*, 1997, vol. 130, pp. 87–92.

Steegmans, P. et al., "Low Serum Cholesterol Concentration and Serotonin Metabolism in Men", *BMJ Cardiol.*, 1996, vol. 312., p. 221.

Heils, A. et al., "Rapid Communication: Allelic Variation of Human Serotonin Transporter Gene Expression", *Journal of Neurochemistry*, 1996, vol. 66, No. 6, pp. 2621–2624.

Lesch, K. et al., "Primary Structure of the Human Platelet Serotonin Uptake Site: Identity with the Brain Serotonin Transporter", *Journal of Neurochemistry*, 1993, vol. 60, No. 6, pp. 2319–2322.

* cited by examiner

*Primary Examiner*—Lisa B. Arthur
*Assistant Examiner*—Jeanine Goldberg
(74) *Attorney, Agent, or Firm*—Rothwell, Figg, Ernst & Manbeck, P.C.

(57) ABSTRACT

Disclosed are methods for screening subjects to determine their risk for developing cardiovascular disease, screening methods to determine potential longevity, therapeutic methods and compositions for treating patients at risk for developing cardiovascular disease, and screening methods for identifying materials useful in the therapeutic methods.

17 Claims, 2 Drawing Sheets

```
AAGCTTGTTGGGGATTCTCCCGCCTGGCGTTGCCGCTCTGAATGCCAGCACCTAACCCCTAATGTCCCTACTGCAGCCTC
|---|---|---|---|---|---|---|---|---|---|---|---|---|---|---|---|  80
TTCGAACAACCCCTAAGAGGGCGGACCGCAACGGCGAGACTTACGGTCGTGGATTGGGGATTACAGGGATGACGTCGGAG

CCAGCATCCCCCCTGCAACCTCCCAGCAACTCCCTGTACCCCTCCTAGGATCGCTCCTGCATCCCCCATTATCCCCCCCT
|---|---|---|---|---|---|---|---|---|---|---|---|---|---|---|---|  160
GGTCGTAGGGGGGACGTTGGAGGGTCGTTGAGGGACATGGGGAGGATCCTAGCGAGGACGTAGGGGGTAATAGGGGGGGA

TCACTCCTCGCGGCATCCCCCCTGCACCCCCCAGCATCCCCCCTGCAGCCCCCCCAGCATCTCCCCTGCACCCCCAGCAT
|---|---|---|---|---|---|---|---|---|---|---|---|---|---|---|---|  240
AGTGAGGAGCGCCGTAGGGGGGACGTGGGGGGTCGTAGGGGGGACGTCGGGGGGGTCGTAGAGGGGACGTGGGGGTCGTA

[=============DELETION=============]
CCCCCCTGCAGCCCTTCCAGCATCCCCCTGCACCTCTCCCAGGATCTCCCCTGCAACCCCCATTATCCCCCCTGCACCCC
|---|---|---|---|---|---|---|---|---|---|---|---|---|---|---|---|  320
GGGGGGACGTCGGGAAGGTCGTAGGGGACGTGGAGAGGGTCCTAGAGGGGACGTTGGGGGTAATAGGGGGGACGTGGGG

TCGCAGTATCCCCCCTGCACCCCCCAGCATCCCCCCATGCACCCCCGGCATCCCCCCTGCACCCCTCCAGCATTCTCCTT
|---|---|---|---|---|---|---|---|---|---|---|---|---|---|---|---|  400
AGCGTCATAGGGGGACGTGGGGGGTCGTAGGGGGTACGTGGGGCCGTAGGGGGACGTGGGAGGTCGTAAGAGGAA

GCACCCTACCAGTATTCCCCCGCATCCCGGCCTCCAAGCCTCCCGCCCACCTTGCGGTCCCCGCCCTGGCGTCTAGGTGG
|---|---|---|---|---|---|---|---|---|---|---|---|---|---|---|---|  480
CGTGGGATGGTCATAAGGGGGCGTAGGGCCGGAGGTTCGGAGGGCGGGTGGAACGCCAGGGGCGGGACCGCAGATCCACC

CACCAGAATCCCGCGCGGACTCCACCCGCTGGGAGCTGCCCTCGCTTGCCCGTGGTTGTCCAGCTCAGTCCCTCTAGACG
|---|---|---|---|---|---|---|---|---|---|---|---|---|---|---|---|  560
GTGGTCTTAGGGCGGGCCTGAGGTGGGCGACCCTCGACGGGAGCGAACGGGCACCAACAGGTCGAGTCAGGGAGATCTGC

CTCAGCCTCGACCTCCCGGGCTCAGCTGATCCTCCACCTCAGCCTCCTGAGTAGCTGGGAACACAAGCGCGAGCAACCAC
|---|---|---|---|---|---|---|---|---|---|---|---|---|---|---|---|  640
GAGTCGGAGCTGGAGGGCCCGAGTCGACTAGGAGGTGGAGTCGGAGGACTCATCGACCCTTGTGTTCGCGCTCGTTGGTG
```

ASSOCIATION OF THE SEROTONIN TRANSPORT (HTT) GENE WITH CARDIOVASCULAR DISEASE AND LONGEVITY

CROSS-REFERENCES TO RELATED APPLICATIONS

This application is the national stage of PCT/US99/03700 filed Feb. 19, 1999, which claims the benefit of U.S. Provisional Application No. 60/110,150 filed Nov. 25, 1998, and U.S. Provisional Application No. 60/075,613 filed Feb. 20, 1998.

STATEMENT REGARDING FEDERALLY SPONSORED RESEARCH OR DEVELOPMENT

Not applicable.

BACKGROUND OF THE INVENTION

1. Field of the Invention

The present invention relates to the association between the serotonin transporter (HTT) gene and serum cholesterol levels, heart disease and longevity.

2. Description of the Related Art

The full citations of the publications referred to herein are found at the end of the specification. The contents of the references are incorporated herein by reference.

Low cholesterol levels have been reported to be associated with the development of depression and violent death by suicide, especially in the elderly (1–5). This occurs both in subjects in the general population and subjects whose cholesterol levels have been lowered by medication. Several possible mechanisms for these phenomena have been suggested including a decrease in serotonin levels (3, 6) or a decrease in the number of membrane serotonin receptors or transporters due to the effect of low cholesterol on membrane fluidity (6). A link between serotonin levels and cholesterol was supported by studies in monkeys showing that those with cholesterol levels altered by diet showed a positive correlation between plasma cholesterol level and central serotonergic activity (7, 8). By contrast, a study by Fernstron, et al. (9) found no significant differences in tryptophan, serotonin or 5-HIAA concentrations in several brain regions in gerbils with a wide range of diet induced variations in cholesterol level.

Steegmans, et al. (10) reported a significant decrease in plasma serotonin, but not platelet serotonin, in 100 men in the general population with a demonstrated long term (3 years) cholesterol level below the fifth percentile compared to 100 control men with cholesterol levels in the 35th to 75th percentile. Smith and Betteridge (11) observed a significant negative correlation between platelet serotonin and cholesterol levels in subjects with hypercholesterolemia and controls (r for both combined=–0.48, p≦0.005). In the hypercholesterolemic subjects there was a significant positive correlation with high-density lipoprotein (HDL) (r=0.79, p=0.001). They concluded there was a significant relationship between circulating cholesterol and platelet serotonin and that a serotonin uptake (transporter) mechanism was involved. Others have suggested the apparent association between low cholesterol and depression could be due to the fact that both were related to a third confounding factor, such as general poor health (12).

The observations that low cholesterol levels induced by medication or diet can be associated with depression suggest that environmental factors are involved and that the low cholesterol was the primary event while the altered serotonin levels were secondary. However, the observation that low cholesterol levels in individuals in the general population can be associated with low serotonin levels and depression is compatible with the possibility that in some cases genetic factors could be responsible for either the low cholesterol, the depression, or both. The fact that elderly subjects are often involved suggests that some variables may be related to age. There is also a well documented association between depression and cardiovascular disease in general (13).

BRIEF SUMMARY OF THE INVENTION

In one aspect, the present invention relates to a method for screening a subject to determine whether such subject is at increased risk for developing cardiovascular disease, said method comprising determining the subject's genotype with respect to the serotonin transport (HTT) gene, wherein an LS heterozygote for the HTTLPR insertion/deletion polymorphism at the promoter region of the HTT gene has an increased risk for developing said disease.

In another aspect, the present invention relates to a method for screening a subject to determine whether such subject is a candidate for a therapy using a drug which prevents or treats a cardiovascular disease associated with excessive production of the serotonin transport protein, said method comprising determining the subject's genotype with respect to the serotonin transport (HTT) gene, wherein an LS heterozygote for the HTTLPR insertion/deletion polymorphism at the promoter region of the HTT gene is a candidate for such therapy.

In another aspect, the present invention provides a method for screening a subject to determine the potential longevity of such subject, said method comprising determining the subject's genotype with respect to the serotonin transport (HTT) gene, wherein an SS homozygote for the HTTLPR insertion/deletion polymorphism at the promoter region of the HTT gene has a greater probability of survival past eighty years of age.

In another aspect, the present invention relates to a method for treating a patient at increased risk for developing cardiovascular disease due to the patient being LS heterozygous for the HTTLPR insertion/deletion polymorphism at the promoter region of the serotonin transport (HTT) gene, said method comprising administering to said patient an effective amount of a material which diminishes the effect of the serotonin transporter protein.

In another aspect, the present invention relates to a method for identifying materials that can be used in the treatment of a patient at increased risk for developing cardiovascular disease due to the patient being LS heterozygous for the HTTLPR insertion/deletion polymorphism at the promoter region of the serotonin transport (HTT) gene, said method comprising determining whether the material is capable of diminishing the effect of the serotonin transporter protein.

In another aspect, the present invention relates to a pharmaceutical composition which comprises a) an effective amount of a material which is capable of diminishing the effect of the serotonin transporter protein in a patient being LS heterozygous for the HTTLPR insertion/deletion polymorphism at the promoter region of the serotonin transport (HTT) gene; and b) a pharmaceutically acceptable carrier.

In another aspect, the present invention relates to a kit suitable for screening a subject to determine whether such subject is at increased risk for developing cardiovascular disease, said kit comprising a) means for determining the subject's genotype with respect to the insertion/deletion polymorphism at the promoter region of the serotonin transport gene;
b) suitable packaging material; and optionally
c) instructional material for use of said kit.

BRIEF DESCRIPTION OF THE DRAWINGS

FIG. 2 shows a partial sequesnce of the regulatory region of the serotonin transporter gene. [SEQ. ID. NO: 5]

DETAILED DESCRIPTION OF THE INVENTION

Figure 1:
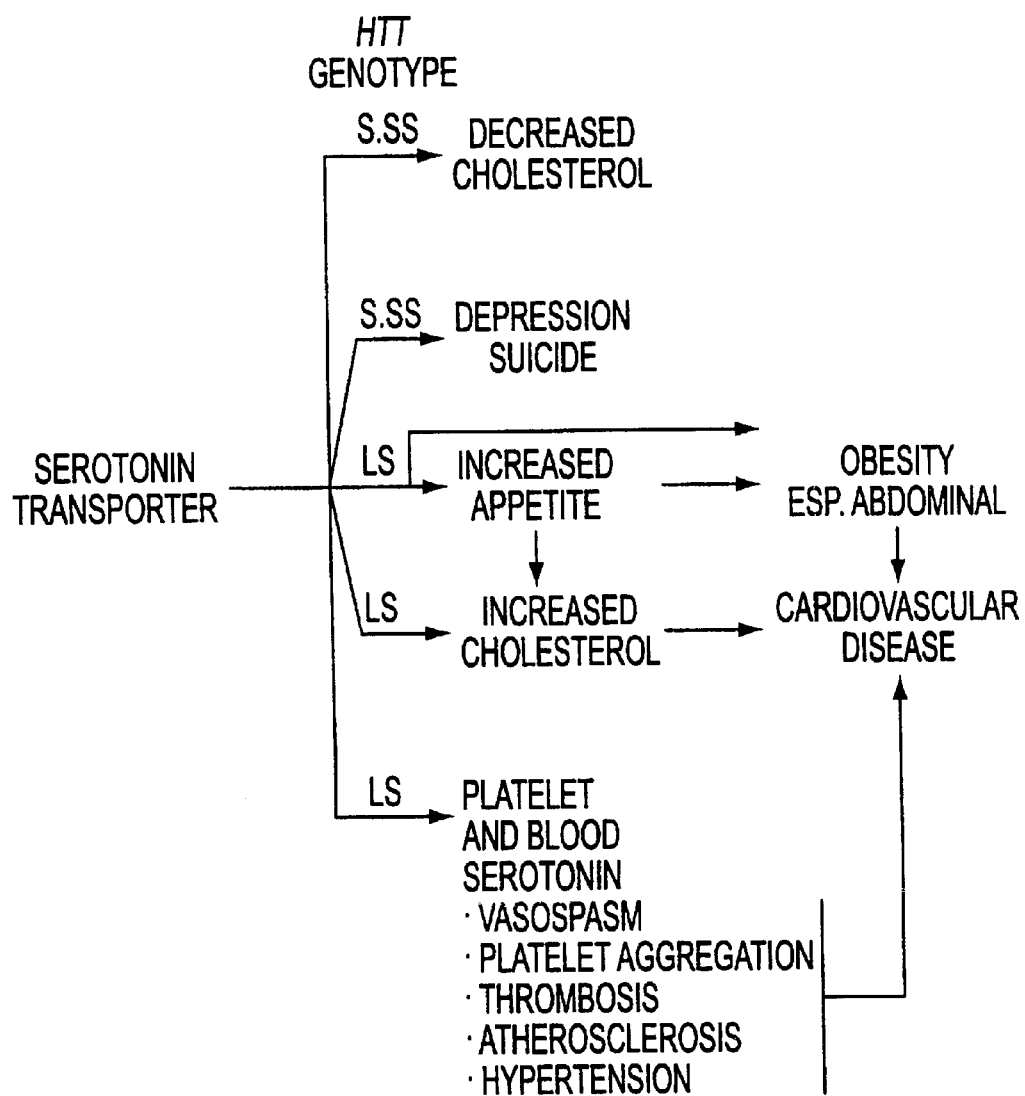
FIG. 1 shows the postulated relationships between the HTT genotypes, cholesterol, depression, and cardiovascular disease.

The present invention is based on the observation that subjects having the LS heterozygote for the insertion/deletion polymorphism in the promoter region of the serotonin transporter (HTT) gene have an increased risk of developing cardiovascular disease, such as elevated cholesterol, angina and heart attacks. Additionally, subjects having the SS homozygote have a greater probability of survival past eighty years of age.

The present invention entails the determination of the subject's genotype with respect to the insertion/deletion polymorphism of the HTT gene described above. Such can be determined, for example, by analysis of the subject's DNA, RNA, or protein, with DNA analysis being particularly preferred. Suitable analysis techniques are well known to those in the art, and include amplification genotyping (amplification of the desired region by suitable methods, such as PCR, followed by electrophoresis), in situ hybridization techniques, direct DNA sequencing, etc.

The L and S alleles of the human serotonin gene which are detected in practice of the present invention are described in reference 1, the contents of which are incorporated herein by reference. The relevant portion of the sequence is shown in FIG. 2 herein. The L allele is shown, and the portion of that allele which is deleted in the S allele is indicated under "Deletion". The complete protein and cDNA sequences are reported (*J. Neural Transm.* 91, 67–73 (1993), incorporated herein by reference) as follows:

/translation=
"METTPLNSQKQLSACEDGEDCQENGV-
LQKVVPTPGDKVESGQIS NGYSAVPSPGAGD-
DTRHSIPATTTTLVAELHQGERETWGKKVDFLL
SVIGYAVDLGNV WRFPYICYQNGGGAFLLPYTI-
MAIFGGIPLFYMELALGQYHRNGCISI-
WRKICPIFKG IGYAICIIAFYIASYYNTIMAWA-
LYYLISSFTDQLPWTSCKNSWNTGNCTNYFS
EDNI TWTLHSTSPAEEFYTRHVLQIHR-
SKGLQDLGGISWQLALCIMLIFTVIYF-
SIWKGVKT SGKVVWVTATFPYIILSVLLVR-
GATLPGAWRGVLFYLKPNWQKLLETGVWID
AAAQIF FSLGPGFGVLLAFASYNK-
FNNNCYQDALVTSVVNCMTSFVSGFV-
IFTVLGYMAEMRNE DVSEVAKDAGPSLL-
FITYAEAIANMPASTFFAIIFFLMLITLGLDSTFA
GLEGVITAV LDEFPHVWAKRRERFVLAV-
VITCFFGSLVTLTFGGAYVVKLLEEYAT-
GPAVLTVALIE AVAVSWFYGITQFCRDVKEMLG-
FSPGWFWRICWVAISPLFLLFIICSFLMSPPQLRLF
QYNYPYWSIILGYCIGTSSFICIPTY-
IAYRLIITPGTFKERIIKSITPETPTEIPCGDI
RLNAV" [SEQ ID NO:1]

BASE COUNT 459a 574c 541g 525t
ORIGIN
1 GCGTGCAACC CGACGATAGA GAGCTCGGAG GTGATCCACA AATCCAAGCA CCCCA-GAGATC
61 CATTGGGATC CTTGGCAGAT GGACATCAGT GTCATTTACT AACCAGCAGG ATGGAGACGA
121 CGCCCTTGAA TTCTCAGAAG CAGCTAT-CAG CGTGTGAAGA TGGAGAAGAT TGTCAG-GAAA
181 ACGGAGTTCT ACAGAAGGTT GTTC-CCACCC CAGGGGACAA AGTGGAGTCC GGGCAAATAT
241 CCAATGGGTA CTCAGCAGTT CCAAGTC-CTG GTGCGGGAGA TGACACACGG CACTC-TATCC
301 CAGCGACCAC CACCACCCTA GTGGCT-GAGC TTCATCAAGG GGAACGGGAC ACCTGGGGCA
361 AGAAGGTGGA TTTCCTTCTC TCAGT-GATTG GCTATGCTGT GGACCTGGGC AAT-GTCTGGC
421 GCTTCCCCTA CATATGTTAC CAGAATGGAG GGGGGGCATT CCTCCTCCCC TACACCATCA
481 TGGCCATTTT TGGGGGAATC CCGCTCTTTT ACATGGAGCT CGCACTGGGA CAGTACCACC
541 GAAATGGATG CATTTCAATA TGGAG-GAAAA TCTGCCCGAT TTTCAAAGGG ATTG-GTTATG
601 CCATCTGCAT CATTGCCTTT TACATTGCTT CCTACTACAA CACCATCATG GCCTGGGCGC
661 TATACTACCT CATCTCCTCC TTCACGGACC AGCTGCCCTG GACCAGCTGC AAGAACTCCT
721 GGAACACTGG CAACTGCACC AATTACT-TCT CCGAGGACAA CATCACCTGG ACCCTC-CATT
781 CCACGTCCCC TGCTGAAGAA TTTTA-CACGC GCCACGTCCT GCAGATCCAC CGGTCTAAGG
841 GGCTCCAGGA CCTGGGGGGC ATCAGCTGGC AGCTGGCCCT CTGCATCATG CTGATCTTCA
901 CTGTTATCTA CTTCAGCATC TGGAAAGGCG TCAAGACCTC TGGCAAGGTG GTGTGGGTGA
961 CAGCCACCTT CCCTTATATC ATCCTTTCTG TCCTGCTGGT GAGGGGTGCC ACCCTCCCTG
1021 GAGCCTGGAG GGGTGTTCTC TTCTACT-TGA AACCCAATTG GCAGAAACTC CTG-GAGACAG
1081 GGGTGTGGAT AGATGCAGCC GCTCA-GATCT TCTTCTCTCT TGGTCCGGGC TTTGGGGTCC
1141 TGCTGGCTTT TGCTAGCTAC AACAAGT-TCA ACAACAACTG CTACCAAGAT GCCCTG-GTGA
1201 CCAGCGTGGT GAACTGCATG ACGAGCT-TCG TTTCGGGATT TGTCATCTTC ACAGT-GCTCG
1261 GTTACATGGC TGAGATGAGG AATGAA-GATG TGTCTGAGGT GGCCAAAGAG GCAG-GTCCCA
1321 GCCTCCTCTT CATCACGTAT GCA-GAAGCGA TAGCCAACAT GCCAGCGTCC ACTTTCTTTG

1381 CCATCATCTT CTTTCTGATG TTAATCACGC TGGGCTTGGA CAGCACGTTT GCAGGCTTGG
1441 AGGGGGTGAT CACGGCTGTG CTGGATGAGT TCCCACACGT CTGGGCCAAG CGCCGGGAGC
1501 GGTTCGTGCT CGCCGTGGTC ATCACCTGCT TCTTTGGATC CCTGGTCACC CTGACTTTTG
1561 GAGGGGCCTA CGTGGTGAAG CTGCTGGAGG AGTATGCCAC GGGGCCCGCA GTGCTCACTG
1621 TCGCGCTGAT CGAAGCAGTC GCTGTGTCTT GGTTCTATGG CATCACTCAG TTCTGCAGGG
1681 ACGTGAAGGA AATGCTCGGC TTCAGCCCGG GGTGGTTCTG GAGGATCGC TGGGTGGCCA
1741 TCAGCCCTCT GTTTCTCCTG TTCATCATTT GCAGTTTTCT GATGAGCCCG CCACAACTAC
1801 GACTTTTCCA ATATAATTAT CCTTACTGGA GTATCATCTT GGGTTACTGC ATAGGAACCT
1861 CATCTTTCAT TTGCATCCCC ACATATATAG CTTATCGGTT GATCATCACT CCAGGGACAT
1921 TTAAAGAGCG TATTATTAAA AGTATTACCC CGGAGACACC AACAGAAATT CCTTGTGGGG
1981 ACATCCGCTT GAATGCTGTG TAACACACTC ACCGAGAGGA AAAAGGCTTC TCCACAACCT
2041 CCTCCTCCAG TTCTGAGGAG GCACGCCTGC CTTCTCCCCT CCGAGTGAAT GAGTTTGCC [SEQ ID NO:2]

A further aspect of the present invention is the treatment of LS heterozygote patients at increased risk for developing cardiovascular disease to prevent the development or progression of such disease. The patient is administered an effective amount of a material which diminishes or eliminates the adverse effects of the serotonin transport protein produced by the patient. The material may act in a number of ways which would be apparent to one of ordinary skill. For example, it may act to decrease the production of the protein, such as by affecting the DNA or RNA responsible for protein production, or by affecting regulatory elements. One way to accomplish diminished protein production is by introduction via gene therapy or gene repair techniques of a gene or gene segment which converts an L allele into either the S allele as described herein, or an allele having the same function as the S allele. See, for example, the techniques described in U.S. Pat. No. 5,776,744, the contents of which are incorporated herein by reference. The material may also act by directly or indirectly affecting the produced protein to diminish the protein's activity or effect.

It will be apparent that the information regarding a subject's genotype with respect to the HTT gene may also be used to determine whether the subject is a candidate for a therapy using a drug which prevents or treats cardiovascular disease caused by excessive production of the serotonin transport protein.

For therapeutic treatment, the materials of the present invention may be formulated into a pharmaceutical composition, which may include, in addition to an effective amount of the active ingredient, pharmaceutically acceptable carriers, diluents, buffers, preservatives, surface active agents, and the like. Compositions may also include one or more other active ingredients if necessary or desirable.

The pharmaceutical compositions of the present invention may be administered in a number of ways as will be apparent to one of ordinary skill in the art. Administration may be done topically, orally, by inhalation, or parenterally, for example.

Topical formulations may include ointments, lotions, creams, gels, drops, suppositories, sprays, liquids and powders. Oral formulations include powders, granules, suspensions or solution in water or non-aqueous media, capsules or tablets, for example. Thickeners, flavorings, diluents, emulsifiers, dispersing aids or binders may be used as needed.

Parenteral formulations may include sterile aqueous solutions which may also contain buffers, diluents and other suitable additives.

The dose regimen of the compounds or compositions of the present invention will depend on a number of factors which may readily be determined, such as severity and responsiveness of the condition to be treated.

The present invention also provides a screening method for identifying materials that may be used in the treatment of a patient at increased risk for developing cardiovascular disease due to the patient being LS heterozygous for the HTTLPR insertion/deletion polymorphism at the promoter region of the serotonin transport (HTT) gene. In practice of such a method, a candidate material is screened in an assay which determines whether the material is capable of diminishing the effect of the serotonin transporter protein. Suitable assays would be readily apparent to one of ordinary skill, including animal models and in vitro assays. The assays may be designed to test, for example, the effect of the material on the production of the serotonin transport protein, or its effect on the activity of the protein.

The present invention also provides a kit suitable for screening a subject for any of the purposes described above (i.e., to determine whether such subject is at increased risk for developing cardiovascular disease; to determine the potential longevity of such subject; or to determine whether such subject is a candidate for the drug therapy described above). The kit comprises means for determining the subject's genotype with respect to the insertion/deletion polymorphism at the promoter region of the serotonin transport gene. Preferably, such means comprise at least two primers capable of hybridizing to a region flanking the HTTLPR insertion/deletion polymorphism at the promoter region of the serotonin transport gene. The primers preferably are suitable for use in an amplification reaction, such as PCR. The kit additionally contains suitable packaging material, and optionally contains instructional material for use of the kit, result interpretation, etc. The kit may also contain additional reactants suitable for use with the primers, such as appropriate concentrations of deoxynucleotide triphosphates, suitable buffers, polymerization enzymes, etc.

The following non-limiting example is illustrative of the processes of the present invention.

EXAMPLE 1

The present study incorporated the following aspects. We had a unique opportunity to examine the potential role of genetic factors in the regulation of cholesterol levels in a healthy but elderly population of men by utilizing the participants in the Golden Games. This is a group of men over 55 years of age, who each year compete in a series of athletic competitions. Cholesterol levels and a history of the presence or absence of heart disease, angina, and heart attack, were available on these subjects (the GG group). As a replication group we also had available a group of subjects in good general health from the Loma Linda University Center for Health Promotion (the CHP group). Cholesterol and triglyceride levels were available on these subjects. As an additional replication group we examined a third group of subjects from Loma Linda University Hospital on whom a history of heart attacks was available (the LLHosp group). Since the subjects in the first two groups were in reasonably good health this minimized the potential role of poor health as a factor in the regulation of cholesterol levels. We examined the serotonin transporter gene (HTT, SLC6A4) since the re-uptake of serotonin plays a role in the regulation of both blood serotonin (re-uptake into platelets) and brain serotonin (re-uptake into presynaptic neurons). A well-characterized insertion (L)/deletion (S) polymorphism (HTTLPR) at the promoter of the HTT gene was utilized since it is known to be associated with variations in HTT gene expression (14). Genetic variants of the HTT gene have been reported to be associated with mood disorders in some (15–19) but not all (20–22) studies. Since elevated cholesterol levels have been reported to be associated with a decreased risk for cardiovascular disease in elderly individuals (23–24), we examined the association between the HTT gene and cholesterol levels in the Golden Games subjects in two age groups 42 to 70 and >70 years of age. (There were too few subjects >70 years of to allow testing in the CHP and LLHosp group.)

The HTT Gene. The promoter of the human 5-hydroxytryptamine (serotonin) transporter gene (HTT) is regulated by an interplay between positive and negative regulatory elements (25). A GC-rich repetitious sequence is located in the proximal 5' regulatory region of the human HTT gene which silences transcriptional activity in nonserotonergic cells, and contains positive response elements (26). Heils, et al. (14) reported a common insertion/deletion polymorphism of this repetitive element. The deletion (short or S allele) was present in approximately one-third of the Caucasian population. Expression studies with a human choriocarcinoma cell line showed that the non-deletion or long or L allele was associated with three times the rate of expression of the serotonin transporter compared to the S allele.

A further relevant aspect is the reported presence of molecular heterosis at the HTT gene (27, 28). Molecular heterosis refers to a situation in which the heterozygotes for a polymorphic gene marker show a greater or lesser phenotypic effect than either homozygote 2S. Little, et al. (27) examined levels of $[^{125}I]\beta$-CIT (citalopram) binding (fmol/mg) to the serotonin transporter in the dorsal and median raphe nuclei and substantia nigra of human controls and subjects with chronic cocaine use. They correlated levels of binding with the genotypes of the SS, LS, and LL alleles of the HTT LPR polymorphism of the HTT gene. This showed that $[^{125}I]\beta$-CIT binding was lower in the LS heterozygotes than either the SS or LL homozygotes in all three regions. A two-way ANOVA was significant for genotype and region and genotype main effect (p<0.001). They also examined serotonin transporter mRNA levels in these three regions. The levels were highest for LL subjects and equally low for LS and SS subjects. Thus, the molecular heterosis effect was specific to an end function of the HTT gene in terms of $[^{125}I]\beta$-CIT binding.

If the association between cholesterol levels and depression was due to a confounding third factor, the HTT gene would qualify as such a factor. The above three groups allowed us to determine if the HTTLPR polymorphism of the HTT gene predicted cholesterol levels, re-test this association for cholesterol and triglycerides, test if the HTT gene was associated with heart attacks, re-test this association, and to determine if the risk was different in the subjects 70 years of age or less versus those over age 70.

Methods

The Golden Games Group. Each year a group of veterans, all of whom are over 55 years of age, compete in an athletic competition called the Golden Games. It is held in a different city each year and the participants are amenable to medical studies including blood drawing. The year that the Golden Games were held in Southern California we obtained blood samples for DNA and cholesterol testing. Of the 100 subjects in the present study, 74 percent were non-Hispanic Caucasian, 18 percent were African-American, and 8 percent were Hispanic or other. They ranged in age from 25 to 91 years. The mean age of the 58 subjects in the ≦70 age group was 63.9 years (S.D. 4.1 years). The mean age of the 42 subjects in the >70 age group was 74.8 (S.D. 3.1). Subjects were questioned about the presence of a history of angina, heart attacks or hypertension. In addition to coding for the presence or absence of each disorder, subjects were also coded for the number of different cardiovascular disease problems and this allowed the scoring of the "heart disease" variable.

The Center for Health Promotion Group (CHP). The subjects from the CHP study consisted of 102 non-Hispanic Caucasians from the Loma Linda University Center for Health Promotion. The age, sex, weight, height, and waist-hip ratio were determined on each subject. The subjects ranged in age from 42 to 70 years of age with a mean age of 55.4 years (S.D. 7.5 years). A fasting blood sample was obtained for determination of cholesterol and triglycerides. The recruitment particularly targeted staff members of the Loma Linda University, and Loma Linda University Medical Center.

The Loma Linda Smoking Group. The subjects from the LLHosp group consisted of a random sample of 83 non-Hispanic Caucasian male inpatients from the Jerry L. Pettis Memorial Veterans Administration Center, Loma Linda, Calif., acquired from a range of hospital wards. They consisted of individuals 42 to 74 years of age with a mean age of 57.0 years (S.D. 8.87 years). There were too few subjects in the >70 age group to analyze separately. Data on the presence or absence of heart attacks were available.

In both studies coded samples of blood were sent to the Department of Medical Genetics at the City of Hope National Medical Center where the genetic studies were performed blind to clinical data. Both studies were approved by the IRBs of both institutions.

Laboratory tests. Cholesterol and triglyceride levels were determined using the REP Ultra-30 HDL, VLDL/LDL Cholesterol system of Helena Laboratories (Beaumont, Tex.). Polymerase chain reaction genotyping of the HTTLPR polymorphism of the HTT gene was performed using conditions and similar primers to those reported by Heils, et al. (14). The forward primer had the following sequence:

GGCGTTGCCG CTCTGAATGC [SEQ ID NO:2].

The reverse primerhad the following sequence:

TGGTAGGGTG CAAGGAGAAT [SEQ ID NO:3].

PCR amplification was carried out in a final volume of 25 $\mu$l containing the sample DNA, 10 mM deoxyribonucleotides, 0.1 mM of each primer, Tris-HCl, KCl, $(NH_4)_2SO_4$, 15 mM $MgCl_2$, 5×Q' solution, and 1.25 U of Taq DNA polymerase. PCR amplification was carried out with an initial denaturation step of 95° C. for 5 minutes, 40 cycles of 95° C. for 30 seconds, 64° C. for 1 minute, and 72° C. for 1 minute, and final reannealing step at 72° C. for 5 minutes. PCR products were run on a 7% (40% 29:1) polyacrylamide gel and visualized with ethidium bromide.

Statistics. The mean cholesterol and triglyceride levels for the different HTT genotypes were compared by ANOVA. The significance levels were determined on the basis of the F-ratio. A post hoc Tukey test indicated those means that were significantly different at α=0.05. Regression analysis of the correlation between cholesterol and triglyceride levels and genotype was performed scoring the HTT gene as LL or SS=0, and LS=1. To examine the percent of the variance for heart attack, heart disease, and angina, their presence was scored as 1, and their absence as 0. This allowed the determination or $r^2$, or the percent of the variance that was attributable to the HTT gene. Chi square analysis was used to compare the number of subjects with a history of heart disease, angina or heart attack in the GG group, and heart attacks in the LLHosp group, versus the LS and LL or SS HTT genotype groups. All statistical analysis was by the SPSS statistical package (SPSS, Inc. Chicago, Ill.).

Results

The results for the 100 Golden Games subjects are shown in Table 1. Since there was no significant difference in the frequencies of the LL, LS, and SS genotypes in the different racial groups, we first examined all races together. The mean cholesterol was 231.41 mg/dl for the LS heterozygotes, versus 197.00 mg/dl for the LL and 206.36 mg/dl for the SS groups ($p \leq 0.0056$). When tested for heterosis by comparing LS heterozygotes to LL+SS homozygotes, the mean cholesterol for the homozygotes was 200.65 mg/dl ($p \leq 0.0017$). When restricted to Caucasians the LS heterozygotes again had the higher mean cholesterol levels but the results were not significant.

When the subjects in the 55 to 70 year old group were examined for all races the mean cholesterol for the LS heterozygotes was 240.00 mg/dl, compared to 190.76 mg/dl for the LL homozygotes, and 201.00 mg/dl for the SS homozygotes ($p \leq 0.0005$). When tested for heterosis by comparing LS heterozygotes to LL+SS homozygotes, the mean cholesterol for the homozygotes was 194.00 mg/dl ($p \leq 0.0001$). When restricted to Caucasians the results were still significant for all three genotypes ($p \leq 0.011$) and for heterozygotes versus homozygotes ($p \leq 0.0026$).

By comparison, when the subjects of all races over age 70 were compared the mean cholesterol for the three groups was similar ($p \leq 0.82$) with the level for the LS heterozygotes being only modestly greater (220.68 mg/dl) than for the homozygotes (210.38 mg/dl) ($p \leq 0.53$). When restricted to Caucasians, the mean cholesterol for the LS heterozygotes was actually lower (210.84 mg/dl) than for the homozygotes (213.57 mg/dl) ($p \leq 0.87$).

In an attempt to replicate these findings, we examined the CHP subjects. In addition to cholesterol levels these subjects also had trigyceride levels. Table 2 shows these results. To allow comparison to the Golden Games yet still have an adequate number of subjects, we examined individuals in the 42 to 70 year age group. There were too few subjects in the >70 year group for statistical analvsis.

The mean cholesterol levels were highest for the LS heterozygotes (218.60 mg/dl), lowest for the LL homozygotes (197.44 mg/dl) and also lower for the SS homozygotes (205.46 mg/dl). While the F-values for all three genotypes were of borderline significance ($p \leq 0.005$) the Tukey test showed that the LS values were significantly higher than the LL values at α=0.05. The test for heterosis by comparison of heterozygotes versus homozygotes was significant ($p \leq 0.019$).

The mean triglyceride levels were also highest for the LS heterozygotes (158.58 mg/dl). The levels for both the LL and SS homozygotes were similar (114.20 mg/dl and 115.20 mg/dl) and lower than for the LS heterozygotes. The F-value for all three genotypes was significant ($p \leq 0.18$). The test for heterosis by comparison of heterozygotes versus homozygotes was significant ($p \leq 0.046$). When sex was used as a covariant it, sex itself was not significant for either cholesterol or triglyceride levels. When BMI was used as a covariant the association between the LS subjects and elevated cholesterol remained significant for both groups ($p<0.001$ for the GG group, $p<0.03$ for the CHP group).

For the Golden Games subjects who were 70 years of age or less, the HTT gene accounted for 23.3 percent of the variance of cholesterol levels, $p \leq 0.0001$; 10.2 percent of the variance for heart attack, $p \leq 0.016$; 9.9 percent of the variance for heart disease, $p \leq 0.018$; and 8.0 percent of the variance for angina, $p \leq 0.034$. For the CHP subjects, the HTT gene accounted for 5.3 percent of the variance of the cholesterol levels ($p \leq 0.019$), and 9.6 percent of the variance of the triglyceride levels ($p \leq 0.0066$).

To examine the hypothesis that the differences we observed by age group might be due to a selection process, we also examined the association between the presence of the HTT genotypes and history of heart disease, angina or heart attack for the two age ranges in the GG group. The results are shown in Table 3. For the GG group subjects less than 70 years of age, the frequencies for those with the respective conditions in those with the LS versus the LL or SS genotype, were as follows: heart disease 68.4% versus 35.1%; angina 42.1% versus 16.2%, and heart attack 42.1% versus 13.5%. The increase in the frequency for those with the LS genotype was significant for all three diagnostic groups ($p \leq 0.016$ to $\leq 0.034$). By comparison, for those over 70 years of age there was no significant difference in the frequency for any of these heart problems in those with the LS genotypes versus the LL or SS genotypes ($p \leq 0.31$ to 1.0).

In an attempt to replicate the association between the HTT alleles and heart attacks, we examined the LLHosp group (Table 3). Here 23.4% of the LS subjects had a history of a heart attack versus 5.6% of the LL or SS subjects ($p>0.030$).

Discussion

Since cholesterol-lowering agents have been reported to be associated with increased violence, depression and suicide, the assumption has been that the changes in cholesterol levels are the primary effect and that changes in serotonin or other neurotransmitters, presumed to be the cause of the behavioral problems, are secondary. The present demonstration of a correlation between genetic variants of the HTT gene and serum cholesterol levels, heart disease, angina, and heart attacks, suggests that the low cholesterol and the increased depression might not be directly related but due to a third confounding factor, genetic variants of the HTT gene. While the mechanism for the association between the HTT gene and depression can be understood to be a result of the effect of the genetic variants on serotonin levels, the mechanism for the association between the HTT gene and cholesterol or triglyceride levels is not intuitively obvious. The following are some of the possible explanations.

1. Serotonin has a direct effect on serum cholesterol levels. This would imply that blood or brain serotonin levels have a direct effect on the synthesis of degradation of cholesterol. We are unaware of such a mechanism.

2. Serotonin has an indirect effect on serum cholesterol levels. There are several possibilities.

a. Genetic variants of the HTT gene have been shown to be associated with mood. If LS heterozygosity was associated with depression, and depression was associated with life style changes that resulted in eating a high cholesterol diet, this could provide an indirect mechanism by which the HTT gene could be associated with high cholesterol levels. The problem with this is that the association we observed between the HTTPRL polymorphism of the HTT gene is far more robust than any reports of an association between this polymorphism and depression.

b. A more likely possibility is that through the well-known effect of serotonin on appetite, genetic variants of the HTT gene could be associated with obesity, which in turn is highly correlated with cholesterol levels. However, the one study of the possible association between the HTTLPR polymorphism and obesity was negative (29). To determine if the HTTLPR polymorphism was associated with weight we examined the association with an age normalized BMI in the CHP aroup. There was a significantly higher BMI (26.0±5.0) in those with the LL genotype compared to those with LS (23.1±4.3) or SS (23.0±5.5) genotypes (p≦0.015). Thus, while these results supported a role of the HTT gene in BMI, they did not support the hypothesis that the association of the LS genotype with elevated cholesterol levels was secondary to greater obesity in these individuals. Since abdominal obesity is most often associated with hypercholesterolemia and heart disease (30) we also examined the association between the HTTLPR polymorphism and the age normalized waist-hip ratios in the CHP group. This ratio was highest for those with the LS genotype (0.89±0.10) compared to those with the LL (0.85±0.09) or the SS (0.86±0.09). However, this was not significant (p≦0.25).

3. The indirect effect is through a third confounding covariant. The identity of this possible confounding covariant is unknown.

When all factors are considered, we believe the most likely explanation for the association between genetic variants of the HR gene and serum cholesterol levels is through the effect of serotonin on appetite and abdominal obesity. However, while a larger series of cases might show a significant correlation between the HR gene and abdominal obesity, as measured by waist:hip ratio, our results suggest it will not be as robust as the association with cholesterol and triglyceride levels. This suggests other factors associated with a more direct effect of the HTT gene on cholesterol levels and heart disease are involved. These potential interactions between genotypes of the HTT gene, cholesterol levels, depression, and cardiovascular disease are summarized in FIG. 1. The LS genotype may exert part of its effect on cholesterol levels and cardiovascular disease through an effect on appetite. There may also be an unknown direct effect on cholesterol levels and on abdominal obesity. Much of the association between the LS genotype and cardiovascular disease may be through the well known role of serotonin on vascular constriction, essential and pulmonary hypertension, platelet aggregation, thrombosis and atheromata formation (31–35). By contrast, the S allele and the SS genotype, may independently exert an effect on serum cholesterol levels and, through its regulation of synaptic serotonin levels, depression.

In addition to the association of the HTTLPR polymorphism with cholesterol and triglyceride levels, the other aspect of interest was the difference in the effect of the HR gene variants on subjects less than 70 years of age versus subjects greater than 70 years of age. This difference was only observed in the Golden Games subjects because they were the only group with a sufficient number of subjects over 70 to have statistical validity. The pattern for cholesterol levels, heart disease, angina, and heart attack were all similar. Thus, the effect was greater for LS heterozygotes for all of these variables only in the less than 70 age aroup. It disappeared or was negative (less effect in the LS heterozygotes) in the over 70 age group. While the number of subjects are still too small for definitive conclusions, we believe the most parsimonious explanation is that the LS heterozygotes who are at greatest risk tend to die at an earlier age. Thus, the LS heterozygotes with elevated cholesterol levels and elevated risk for cardiovascular disease, are missing from the older age group.

A final aspect of this study is the question of whether it is relevant to the apparent association between low cholesterol levels and depression, or to the observation that an elevated cholesterol level becomes less of a risk factor for cardiovascular disease or premature death in older subjects. It would seem that since HTT gene variants are modestly associated with both affective disorders and serum cholesterol, the association between low cholesterol and depression could be due to the HTT gene as a confounding third factor. Based on the present results, the specific hypothesis would be that since LS heterozygosity is associated with elevated cholesterol levels, then LL or SS homozygosity, associated with lower cholesterol levels would be the genotypes associated with depression. The literature suggests this is the case. Those studies that have reported a positive association between the HTTLPR polymorphism and affective disorder have reported the association to be with the SS genotype, or S allele (36). Thus, in population based studies, individuals with the SS genotype would have lower cholesterol levels and greater levels of depression. However, since the S allele is associated with lower rates of synthesis of the 5-HT transporter, this should be associated with elevated levels of synaptic serotonin and less depression. This paradox has been commented on by Collier, et al. (18) and Routledge and Middlemiss (37). The latter authors suggested that the decreased expression of the H17 gene by the S allele results in a modest elevation of raphe serotonin levels, but this produces an enhanced negative feedback via somatodendritic $5\text{-HT}_{1A}$ receptors resulting in an overall decrease in terminal serotonin output.

The second issue is whether the present findings can explain the fact that an elevated cholesterol level is less of a risk factor for cardiovascular disease in older individuals. This decreased risk in older subjects seems to parallel our observation that the association of the LS genotype with elevated cholesterol levels, heart disease, angina, and heart attack also disappeared in the over 70 age group. Our hypothesis that the latter is due to the premature death of LS subjects, and could also explain why elevated cholesterol levels are no longer a risk factor in this age group, i.e. those LS subjects at greatest risk because of elevated levels of cholesterol and an elevated risk for heart disease associated with the HTT gene—die prematurely. Those who are left have elevated cholesterol levels due to non-genetic reasons or different genetic reasons, and in these subjects, perhaps because serotonin is not involved, an elevated cholesterol level per se does not have the same dire consequences. Further studies of the role of other serotonin genes in cardiovascular disease are in progress.

TABLE 1

Association between the Genotypes of the HTT Gene and Serum Cholesterol Levels in Golden Games Males in Two Age Groups

| Genotype | N | Mean (mg/dl) | S.D. | F | p |
|---|---|---|---|---|---|
| Age All races (HTTLPR) (n = 100) | | | | | |
| LL | 39 | 197.00 | 41.45 | | |
| LS | 36 | 231.41* | 48.30 | | |
| SS | 25 | 206.36 | 49.10 | 5.48 | ≦.0056 |
| LL + SS | 64 | 200.65 | 48.30 | | |
| LS | 36 | 231.41 | 48.30 | 10.36 | ≦.0017 |
| Age Caucasians only (HTTLPR) (n = 72) | | | | | |
| LL | 25 | 205.20 | 41.52 | | |
| LS | 27 | 227.63* | 40.82 | | |
| SS | 20 | 208.05 | 53.55 | 1.89 | ≦.158 |
| LL + SS | 45 | 206.46 | 46.69 | | |
| LS | 27 | 227.62 | 47.12 | 3.79 | ≦0.55 |
| Age 55 to 70 All races (HTTLPR) (n = 58) | | | | | |
| LL | 26 | 190.76 | 42.11 | | |
| LS | 20 | 240.00# | 44.05 | | |
| SS | 12 | 201.00 | 28.41 | 8.72 | ≦.0005 |
| LL + SS | 38 | 194.00 | 38.22 | | |
| LS | 20 | 240.00 | 44.05 | 17.07 | ≦.0001 |
| Age 55 to 70 Caucasians only (HTTLPR) (n = 38) | | | | | |
| LL | 16 | 199.37 | 39.95 | | |
| LS | 14 | 243.21 | 44.93 | | |
| SS | 8 | 202.00 | 28.71 | 5.11 | ≦.011 |
| LL + SS | 24 | 200.25 | 35.96 | | |
| LS | 14 | 243.21 | 44.93 | 10.49 | ≦.0026 |
| Age >70 All races (HTTLPR) (n = 42) | | | | | |
| LL | 13 | 209.46 | 38.67 | | |
| LS | 16 | 220.68 | 52.58 | | |
| SS | 13 | 211.31 | 63.45 | .194 | ≦.82 |
| LL + SS | 26 | 210.38 | 51.51 | | |
| LS | 16 | 220.68 | 52.58 | .390 | ≦.53 |
| Age >70 Caucasians only (HTTLPR) (n = 34) | | | | | |
| LL | 9 | 215.55 | 44.60 | | |
| LS | 13 | 210.84 | 28.91 | | |
| SS | 12 | 212.08 | 66.21 | .025 | ≦.97 |
| LL + SS | 21 | 213.57 | 28.91 | | |
| LS | 13 | 210.84 | 28.91 | .025 | ≦.87 |

*Significantly different from LL by Tukey test at α = 05.
Significantly different from LL and SS by Tukey test at α = .05.

TABLE 2

Association between the Genotypes of the HTT Gene and Serum Cholesterol and Triglyceride Levels in CHP Males and Females 42 to 70 years of age (n = 102)

| Genotype | N | Mean (mg/dl) | S.D. | F | p |
|---|---|---|---|---|---|
| Cholesterol | | | | | |
| LL | 34 | 197.44 | 32.98 | | |
| LS | 55 | 218.60* | 43.11 | | |
| SS | 13 | 205.46 | 44.62 | 2.99 | ≦.055 |
| LL + SS | 47 | 199.65 | 36.23 | | |
| LS | 55 | 218.60 | 42.78 | 5.65 | ≦.019 |
| Triglycerides | | | | | |
| LL | 34 | 114.20 | 71.76 | | |
| LS | 55 | 158.58* | 84.03 | | |
| SS | 13 | 115.20 | 53.11 | 4.15 | ≦.018 |
| LL + SS | 47 | 114.55 | 66.56 | | |
| LS | 55 | 158.58 | 84.03 | 8.39 | ≦.0046 |

*Significantly different from LL by Tukey test at α = .05.

TABLE 3

HTT Genotype and History of Angina, Heart Disease or Heart Attack (% yes or no, all 1 d.f.)

| | HTT Genotype | | | |
|---|---|---|---|---|
| Condition | LS | LL + SS | Chi Square | p |
| GOLDEN GAMES | | | | |
| A. Heart disease | | | | |
| Age 55 to 70 All races (HTTLPR) (n = 56) | | | | |
| Yes | 13 (68.4) | 13 (35.1) | | |
| No | 6 (31.6) | 24 (64.9) | 5.59 | ≦.018 |
| Age >70 All races (HTTLPR) (n = 42) | | | | |
| Yes | 8 (50.0) | 13 (50.0) | | |
| No | 8 (50.0) | 13 (50.0) | .000 | ≦1.00 |
| B. Angina | | | | |
| Age 55 to 70 All races (HTTLPR) (n = 56) | | | | |
| Yes | 8 (42.1) | 6 (16.2) | | |
| No | 11 (57.9) | 31 (83.8) | 4.48 | ≦.034 |
| Age >70 All races (HTTLPR) (n = 42) | | | | |
| Yes | 5 (31.3) | 8 (30.8) | | |
| No | 11 (68.8) | 18 (69.2) | .001 | ≦.97 |
| C. Heart attack | | | | |
| Age 55 to 70 All races (HTTLPR) (n - 56) | | | | |
| Yes | 8 (42.1) | 5 (13.5) | | |
| No | 11 (57.9) | 32 (86.5) | 5.75 | ≦.016 |
| Age >70 All races (HTTLPR) (n - 42) | | | | |
| Yes | 6 (37.5) | 6 (23.1) | | |
| No | 10 (62.5) | 20 (76.9) | 1.00 | ≦.31 |
| LLHosp GROUP Heart attack (n = 83) | | | | |
| Yes | 11 (23.4) | 2 (5.6) | | |
| No | 36 (76.6) | 34 (94.4) | 4.91 | ≦.03 |

References

1. Golomb B A. Cholesterol and violence: is there a connection? Ann Int Med 1998; 128: 478–487.
2. Lindberg G, Rastam L, Guilberg B, Eklund G A. Low serum cholesterol concentration and short term mortality from injuries in men and women. BMJ 1992; 305: 277–279.
3. Brown S L, Dalive M E, Harris T B, Simonsick E M, Guralnik J M, Kohout F J. Low cholesterol concentrations and severe depressive symptoms in elderly people. BMJ 1994; 308: 1328–1332.
4. Rozzini R, Bertozzi B, Barbisoni P, Trabucchi M. Low serum cholesterol and sertonin metabolism. Risk of depression is higher in elderly patients with lowest serum cholesterol values. BMJ 1966; 312: 1298–1299.

5. Ainiyet J, Rybakowski J. Low concentration level of total serum cholesterol as a risk factor for suicidal and aggressive behavior. Psychiatr Pol 1996; 30: 499–509.
6. Engelberg H. Low serum cholesterol and suicide. Lancet 1992; 339: 727–729.
7. Kaplan J R, Shively C A, Fontenot M B, et al. Demonstration of an association among dietary cholesterol, central serotonergic activity, and social behavior in monkeys. Psychosom Med 1994; 56: 479–484.
8. Muldoon M, Kaplan J, Manuck S, Mann J. Effects of a low-fat diet on brain serotonergic responsivity in cynomolgus monkeys. Biol Psychiatry 1992; 31: 739–742.
9. Fernstrom M H, Verrico C D, Ebaugh A L, Fernstrom J D. Diet-induced changes in serum cholesterol concentrations do not alter tryptophan hydroxylation rate of serotonin concentrations in gerbil brain. Life Sci 1996; 58: 1433–1444.
10. Steegmans P H A, Fekkes D, Hoes A W, Bak A A A, vender Does E, Grobbee D E. Low serum cholesterol concentration and serotonin metabolism in men. BMJ 1996; 312: 221.
11. Smith C C, Betteridge D J. Reduced platelet serotonin content and release in familial hypercholesterolaemia. Atherosclerosis 1997; 130: 87–92.
12. Brown S L. Cholesterol concentrations and depression in elderly people. Ann Med 1994; 27: 141–142.
13. Musselman D, Eavan D L, Nemeroff C B. The relationship of depression to cardiovascular disease. Arch Gen Psychiatry 1998; 55: 580–592.
14. Heils A, Teuiel A, Petri S, et al. Allelic variation of human serotonin transporter gene expression. J Neurochem 1996; 66: 2621–2624.
15. Ogilvie A D, Battersby S, Bubb V J, et al. Polymorphism in the serotonin transporter gene associated with susceptability to major depression. Lancet 1996; 347: 731–733.
16. Rees M, Norton N, Jones I, et al. Association studies of bipolar disorder at the human serotonin transporter gene (hSERT; 5HTT). Mol Psychiatry 1997; 2: 398–402.
17. Furlong R A, R L, Walsh C, et al. Analysis and meta-analysis of two serotonin transporter gene polymorphisms in bipolar and unipolar affective disorders. Am J Med Gen (Neuropsych Genet) 1998; 81: 58–63.
18. Collier D A, Arranz M J, Sham P, et al. The serotonin transporter is a potential susceptability factor for bipolar affective disorder. NeuroReport 1996; 7: 1675–1679.
19. Rosenthal N E, Mazanti C M, Barnett R L, et al. Role of serotonin transporter promoter repeat length polymorphism (5-HTTLPR) in seasonality and seasonal affective disorder. Mol Psychiatry 1998; 3: 175–177.
20. Kunugi H, Tatsumi M, Sakai T, Hatori M, Nanko S. Serotonin transporter gene polymorphism and affective disorder. Lancet 1996; 347: 1340.
21. Bellivier F, Laplanche J-L, Leboyer M, et al. Serotonin transporter gene and manic depressive illness: An association study. Biol Psychiatry 1997; 41: 750–752.
22. Greenberg B D, McMahon E F, Murphy D L. Serotonin transporter candidate gene studies in affective disorders and personality: promises and potential pitfalls. Mol Psychiatry 1998; 3: 186–189.
23. Curb JD, Schatz I, Grove J, et al. Association of short term mortality with plasma cholesterol in the elderly. Can J Cardiol 1997; Suppl 13: A0101.
24. Weverling-Rijnsburger A W, Blauw G J, Lagaay A M, Knook D L, Meinders A E, Westendorp R G. Total cholesterol and risk of mortality in the oldest old. Lancet 1997; 350: 1119–1123.
25. Lesch K P, Balling U, Gross J, et al. Organization of the human serotonin transporter gene. J Neural Transm Gen Sect 1994; 95: 157–162.
26. Heils A, Teuiel A, Petri S, et al. Functional promoter and polyadenylation site mapping of the human serotonin (5-HT) transporter gene. J Neural Transm 1995; 102: 247–254.
27. Little K Y, McLaughlin D P, Zhang L, et al. Cocaine, ethanol, and genotype effects on human midbrain serotonin transporter binding sites and mRNA levels. Am J Psychiatry 1998; 155: 207–213.
28. Comings D E, MacMurray J M. Molecular Heterosis: A Review. Am J Med Gen (Neuropsych Genet) 1998; (submitted)
29. Hinney A, Barth N, Ziegler A, et al. Serotonin transporter gene-linked polymorphic region: allele distributions in relationship to body weight and in anorexia nervosa. Life Sci 1997; 61: PL 295-PL 303.
30. Larsson B, Svardsudd K, Welin L, Wilhelmsen L, Bjorntorp P, Tibblin G. Abdominal adipose tissue distribution, obesity, and risk of cardiovascular disease and death: 13 year follow up of participants in the study of men born in 1913. Br Med J (Clin Res Ed) 1984; 288: 1401–1404.
31. Yildiz O, Smith J R, Purdy R E. Serotonin and vasoconstrictor synergism. Life Sci 1998; 62: 1723–1732.
32. De Clerck F. The role of serotonin in thrombogenesis. Clin Physiol Biochem 1990; 8 Suppl 3:40–49.
33. Vanhoutte P, Amery A, Birkenhager W, et al. Serotoninergic mechanisms in hypertension. Focus on the effects of ketanserin. Hypertension 1988; 11:111–133.
34. Amstein R, Fetkovska N, Luscher T F, Kiowski W, Buhler F R. Age and the platlet serotonin vasoconstrictor axis in essential hypertension. J Cardiovasc Pharmacol 1988; 11 Suppl 1: S35–S40.
35. Vanhoutte P M. Serotonin, hypertension and vascular disease. Neth J Med 1991; 38:35–42.
36. Collier D A, Stober G, Li T, et al. A novel functional polymorphism within the promoter of the serotonin transporter gene: possible role in susceptibility to affective disorders. Molecular Psychiatry 1996; 1: 453–460.
37. Routledge C, Middlemiss D N. The 5-HT hypothesis of depression revisited. Molecular Psychiatry 1996; 1:437.

What is claimed is:

1. A method for screening a subject for determining whether said subject is at an increased risk for developing elevated cholesterol, said method comprising determining the subject's HTTLPR insertion/deletion polymorphism genotype within the serotonin transport (HTT) gene, wherein an LS heterozygote for the HTTLPR insertion/deletion polymorphism in the promoter region of the HTT gene has an increased risk for developing elevated cholesterol.

2. The method of claim 1, wherein said analysis is performed by sequencing.

3. The method of claim 1, wherein said analysis is performed by amplification of at least a portion of the promotor region.

4. The method of claim 1, wherein said analysis is performed by a hybridization reaction.

5. The method of claim 4, wherein the hybridization reaction is an in situ hybridization.

6. A method for screening a subject for determining whether said subject is at an increased risk for developing angina, said method comprising determining the subject's HTTLPR insertion/deletion polymorphism genotype within the serotonin transport (HTT) gene, wherein an LS heterozygote for the HTTLPR insertion/deletion polymorphism in the promoter region of the HTT gene has an increased risk for developing angina.

7. The method of claim 6, wherein the subject is less than 70 years of age.

8. The method of claim 6, wherein said analysis is performed by sequencing.

9. The method of claim 6, wherein said analysis is performed by amplification of at least a portion of the promotor region.

10. The method of claim 6, wherein said analysis is performed by a hybridization reaction.

11. The method of claim 10, wherein the hybridization reaction is an in situ hybridization.

12. A method for screening a subject for determining whether said subject is at an increased risk for having a heart attack, said method comprising determining the subject's HTTLPR insertion/deletion polymorphism genotype within the serotonin transport (HTT) gene, wherein an LS heterozygote for the HTTLPR insertion/deletion polymorphism in the promoter region of the HTT gene has an increased risk for having a heart attack.

13. The method of claim 12, wherein the subject is less than 70 years of age.

14. The method of claim 12, wherein said analysis is performed by sequencing.

15. The method of claim 12, wherein said analysis is performed by amplification of at least a portion of the promotor region.

16. The method of claim 12, wherein said analysis is performed by a hybridization reaction.

17. The method of claim 16, wherein the hybridization reaction is an in situ hybridization.

\* \* \* \* \*

UNITED STATES PATENT AND TRADEMARK OFFICE
CERTIFICATE OF CORRECTION

PATENT NO.     : 6,653,073 B1
DATED          : November 25, 2003
INVENTOR(S)    : Comings et al.

It is certified that error appears in the above-identified patent and that said Letters Patent is hereby corrected as shown below:

Column 9,
Line 58, "0.005" should read -- 0.055 --

Column 10,
Line 2, "0.046" should read -- 0.0046 --
Line 7, "0.001" should read -- 0.0001 --

Signed and Sealed this

Third Day of August, 2004

JON W. DUDAS
*Acting Director of the United States Patent and Trademark Office*

SEQUENCE LISTING

<160> NUMBER OF SEQ ID NOS: 5

<210> SEQ ID NO 1
<211> LENGTH: 630
<212> TYPE: PRT
<213> ORGANISM: Homo sapiens

<400> SEQUENCE: 1

```
Met Glu Thr Thr Pro Leu Asn Ser Gln Lys Gln Leu Ser Ala Cys Glu
  1               5                  10                  15

Asp Gly Glu Asp Cys Gln Glu Asn Gly Val Leu Gln Lys Val Val Pro
             20                  25                  30

Thr Pro Gly Asp Lys Val Glu Ser Gly Gln Ile Ser Asn Gly Tyr Ser
         35                  40                  45

Ala Val Pro Ser Pro Gly Ala Gly Asp Asp Thr Arg His Ser Ile Pro
 50                  55                  60

Ala Thr Thr Thr Thr Leu Val Ala Glu Leu His Gln Gly Glu Arg Glu
 65                  70                  75                  80

Thr Trp Gly Lys Lys Val Asp Phe Leu Leu Ser Val Ile Gly Tyr Ala
             85                  90                  95

Val Asp Leu Gly Asn Val Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
            115                 120                 125

Gly Ile Pro Leu Phe Tyr Met Glu Leu Ala Leu Gly Gln Tyr His Arg
        130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Ile Ala Ser Tyr Tyr
                165                 170                 175

Asn Thr Ile Met Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ser Glu Asp Asn Ile Thr Trp Thr Leu His Ser
210                 215                 220

Thr Ser Pro Ala Glu Glu Phe Tyr Thr Arg His Val Leu Gln Ile His
225                 230                 235                 240

Arg Ser Lys Gly Leu Gln Asp Leu Gly Gly Ile Ser Trp Gln Leu Ala
                245                 250                 255

Leu Cys Ile Met Leu Ile Phe Thr Val Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Ile Leu Ser Val Leu Leu Val Arg Gly Ala Thr Leu Pro Gly
    290                 295                 300

Ala Trp Arg Gly Val Leu Phe Tyr Leu Lys Pro Asn Trp Gln Lys Leu
305                 310                 315                 320

Leu Glu Thr Gly Val Trp Ile Asp Ala Ala Gln Ile Phe Phe Ser
            325                 330                 335

Leu Gly Pro Gly Phe Gly Val Leu Leu Ala Phe Ala Ser Tyr Asn Lys
        340                 345                 350

Phe Asn Asn Asn Cys Tyr Gln Asp Ala Leu Val Thr Ser Val Val Asn
            355                 360                 365

Cys Met Thr Ser Phe Val Ser Gly Phe Val Ile Phe Thr Val Leu Gly
        370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
```

```
                    405                 410                 415
Met Pro Ala Ser Thr Phe Phe Ala Ile Ile Phe Phe Leu Met Leu Ile
                420                 425                 430

Thr Leu Gly Leu Asp Ser Thr Phe Ala Gly Leu Glu Gly Val Ile Thr
            435                 440                 445

Ala Val Leu Asp Glu Phe Pro His Val Trp Ala Lys Arg Arg Glu Arg
        450                 455                 460

Phe Val Leu Ala Val Val Ile Thr Cys Phe Phe Gly Ser Leu Val Thr
465                 470                 475                 480

Leu Thr Phe Gly Gly Ala Tyr Val Val Lys Leu Leu Glu Glu Tyr Ala
                485                 490                 495

Thr Gly Pro Ala Val Leu Thr Val Ala Leu Ile Glu Ala Val Ala Val
            500                 505                 510

Ser Trp Phe Tyr Gly Ile Thr Gln Phe Cys Arg Asp Val Lys Glu Met
        515                 520                 525

Leu Gly Phe Ser Pro Gly Trp Phe Trp Arg Ile Cys Trp Val Ala Ile
    530                 535                 540

Ser Pro Leu Phe Leu Leu Phe Ile Ile Cys Ser Phe Leu Met Ser Pro
545                 550                 555                 560

Pro Gln Leu Arg Leu Phe Gln Tyr Asn Tyr Pro Tyr Trp Ser Ile Ile
                565                 570                 575

Leu Gly Tyr Cys Ile Gly Thr Ser Ser Phe Ile Cys Ile Pro Thr Tyr
            580                 585                 590

Ile Ala Tyr Arg Leu Ile Ile Thr Pro Gly Thr Phe Lys Glu Arg Ile
        595                 600                 605

Ile Lys Ser Ile Thr Pro Glu Thr Pro Thr Glu Ile Pro Cys Gly Asp
    610                 615                 620

Ile Arg Leu Asn Ala Val
625                 630

<210> SEQ ID NO 2
<211> LENGTH: 2099
<212> TYPE: DNA
<213> ORGANISM: Homo sapiens

<400> SEQUENCE: 2
gcgtgcaacc cgacgataga gagctcggag gtgatccaca aatccaagca cccagagatc     60
cattgggatc cttggcagat ggacatcagt gtcatttact aaccagcagg atggagacga    120
cgcccttgaa ttctcagaag cagctatcag cgtgtgaaga tggagaagat tgtcaggaaa    180
acggagttct acagaaggtt gttcccaccc caggggacaa agtggagtcc gggcaaatat    240
ccaatgggta ctcagcagtt ccaagtcctg gtgcgggaga tgacacacgg cactctatcc    300
cagcgaccac caccacccta gtggctgagc ttcatcaagg gaacgggag acctggggca    360 agaaggtgga tttccttctc tcagtgattg ctatgctgt ggacctgggc aatgtctggc    420
gcttccccta catatgttac cagaatggag ggggggcatt cctcctcccc tacaccatca    480
tggccatttt tgggggaatc ccgctctttt acatggagct cgcactggga cagtaccacc    540
gaaatggatg catttcaata tggaggaaaa tctgcccgat tttcaaaggg attggttatg    600
ccatctgcat cattgccttt tacattgctt cctactacaa caccatcatg gcctgggcgc    660
tatactacct catctcctcc ttcacggacc agctgccctg gaccagctgc aagaactcct    720
ggaacactgg caactgcacc aattacttct ccgaggacaa catcacctgg accctccatt    780
ccacgtcccc tgctgaagaa ttttacacgc gccacgtcct gcagatccac cggtctaagg    840
```

```
ggctccagga cctgggggc atcagctggc agctggccct ctgcatcatg ctgatcttca    900
ctgttatcta cttcagcatc tggaaaggcg tcaagacctc tggcaaggtg gtgtgggtga    960
cagccacctt cccttatatc atcctttctg tcctgctggt gagggtgcc accctccctg   1020
gagcctggag gggtgttctc ttctacttga aacccaattg gcagaaactc ctggagacag   1080
gggtgtggat agatgcagcc gctcagatct tcttctctct tggtccgggc tttggggtcc   1140
tgctggcttt tgctagctac aacaagttca caacaactg ctaccaagat gccctggtga   1200
ccagcgtggt gaactgcatg acgagcttcg tttcgggatt tgtcatcttc acagtgctcg   1260
gttacatggc tgagatgagg aatgaagatg tgtctgaggt ggccaaagac gcaggtccca   1320
gcctcctctt catcacgtat gcagaagcga tagccaacat gccagcgtcc actttctttg   1380
ccatcatctt ctttctgatg ttaatcacgc tgggcttgga cagcacgttt gcaggcttgg   1440
aggggggtgat cacggctgtg ctggatgagt tcccacacgt ctgggccaag cgccgggagc   1500
ggttcgtgct cgccgtggtc atcacctgct tctttggatc cctggtcacc ctgactttt g   1560
gaggggccta cgtggtgaag ctgctggagg agtatgccac ggggcccgca gtgctcactg   1620
tcgcgctgat cgaagcagtc gctgtgtctt ggttctatgg catcactcag ttctgcaggg   1680
acgtgaagga aatgctcggc ttcagcccgg ggtggttctg gaggatctgc tgggtggcca   1740
tcagccctct gtttctcctg ttcatcattt gcagttttct gatgagcccg ccacaactac   1800
gactttttcca atataattat ccttactgga gtatcatctt gggttactgc ataggaacct   1860
catctttcat ttgcatcccc acatatag cttatcggtt gatcatcact ccagggacat   1920
ttaaagagcg tattattaaa agtattaccc cggagacacc aacagaaatt ccttgtgggg   1980
acatccgctt gaatgctgtg taacacactc accgagagga aaaggcttc tccacaacct   2040
cctcctccag ttctgaggag gcacgcctgc cttctcccct ccgagtgaat gagttttgcc   2099
```

<210> SEQ ID NO 3
<211> LENGTH: 20
<212> TYPE: DNA
<213> ORGANISM: Homo sapiens

<400> SEQUENCE: 3

```
ggcgttgccg ctctgaatgc                                                 20
```

<210> SEQ ID NO 4
<211> LENGTH: 20
<212> TYPE: DNA
<213> ORGANISM: Homo sapiens

<400> SEQUENCE: 4

```
tggtagggtg caaggagaat                                                 20
```

<210> SEQ ID NO 5
<211> LENGTH: 640
<212> TYPE: DNA
<213> ORGANISM: Homo sapiens

<400> SEQUENCE: 5

```
aagcttgttg gggattctcc cgcctggcgt tgccgctctg aatgccagca cctaacccct     60
aatgtcccta ctgcagcctc ccagcatccc cctgcaacc tcccagcaac tccctgtacc    120
cctcctagga tcgctcctgc atcccccatt atccccccct tcactcctcg cggcatcccc    180
cctgcacccc ccagcatccc cctgcagcc ccccagcat ctccctgca ccccagcat      240
```

-continued

```
cccccctgca gcccttccag catcccctg cacctctccc aggatctccc ctgcaacccc    300
cattatcccc cctgcacccc tcgcagtatc cccctgcac ccccagcat cccccatgc     360 accccggca tcccctgc accctccag cattctcctt gcacctacc agtattcccc        420 cgcatcccgg cctccaagcc tcccgcccac cttgcggtcc ccgccctggc gtctaggtgg   480
caccagaatc ccgcgcggac tccacccgct gggagctgcc ctcgcttgcc cgtggttgtc   540
cagctcagtc cctctagacg ctcagcctcg acctcccggg ctcagctgat cctccacctc   600
agcctcctga gtagctggga acacaagcgc gagcaaccac                        640
```